United States Patent [19]

Inamoto et al.

[11] 4,168,389
[45] Sep. 18, 1979

[54] 1-ALKOXYTRICYCLO[4.3.1.1$^{2,5}$]UNDEC-ANES

[75] Inventors: Yoshiaki Inamoto; Koji Aigami, both of Wakayama; Naotake Takaishi, Sakura; Motoki Nakajima, Miyashiro-machi, all of Japan

[73] Assignee: Kao Soap Co., Ltd., Tokyo, Japan

[21] Appl. No.: 893,827

[22] Filed: Apr. 6, 1978

[30] Foreign Application Priority Data

Apr. 11, 1977 [JP] Japan .................................. 52/40340

[51] Int. Cl.$^2$ ............................................ C07C 43/18
[52] U.S. Cl. .................. 568/665; 260/648 R; 252/522
[58] Field of Search ..................... 260/611 F; 568/665

[56] References Cited

U.S. PATENT DOCUMENTS 3,383,423  5/1968  Moore .............................. 260/611 F

OTHER PUBLICATIONS

Takaishi et al, Journal of the Chemical Society, Perkin Trans., vol. I, (1975), pp. 789-792.

*Primary Examiner*—Bernard Helfin
*Attorney, Agent, or Firm*—Oblon, Fisher, Spivak, McClelland & Maier

[57] ABSTRACT

1-Alkoxytricyclo[4.3.1.1$^{2,5}$]undecanes having the formula (I),

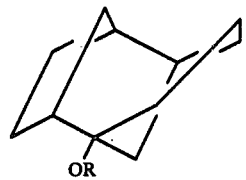

(I)

wherein R represents an alkyl group having 1 to 6 carbon atoms or a cycloalkyl group having 5 to 6 carbon atoms are prepared by a process which comprises reacting 1-halogenotricyclo[4.3.2.1$^{2,5}$]undecanes the formula (II),

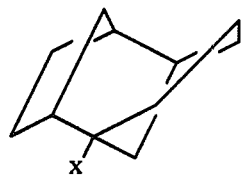

(II)

wherein X is a chlorine or bromine atom, with alcohols of the formula (III),

R-OH  (III)

wherein R is as above defined. A perfume composition comprising an undecane of the formula (I) possesses an excellent odor.

5 Claims, No Drawings

1-ALKOXYTRICYCLO[4.3.1.1$^{2,5}$]UNDECANES

BACKGROUND OF THE INVENTION

This invention relates to a novel tricycloundecanol derivative, more particularly to 1-alkoxytricyclo[4.3.1.1$^{2,5}$]undecane of the formula (I),

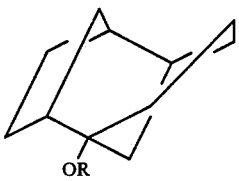

wherein R represents an alkyl group having 1 to 6 carbon atoms or a cycloalkyl group having 5 to 6 carbon atoms, and to a process for producing the undecane, and further to a perfume and flavor composition comprising the undecane.

The carbon framework of the present compound of the formula (I), tricyclo[4.3.1.1$^{2,5}$]undecane, was first isolated as an isomerized intermediate [J.C.S. Perkin Trans., I 789 (1975)] any derivative of which, however, remains unreported.

SUMMARY OF THE INVENTION

The present inventors have examined a wide variety of tricycloundecanol derivatives and have succeeded in synthesizing the 1-alkoxytricyclo[4.3.1.1$^{2,5}$]undecane of the formula (I) possessing an excellent perfume which has never been reported in any literature. The invention has been achieved based on this finding.

DETAILED DESCRIPTION OF THE INVENTION

The 1-alkoxytricyclo[4.3.1.1$^{2,5}$]undecane of the formula (I) according to the invention is produced by reacting 1-halogenotricyclo[4.3.1.1$^{2,5}$]undecane of the formula (II) with alcohols of the formula (III) as is shown by the following reaction formula,

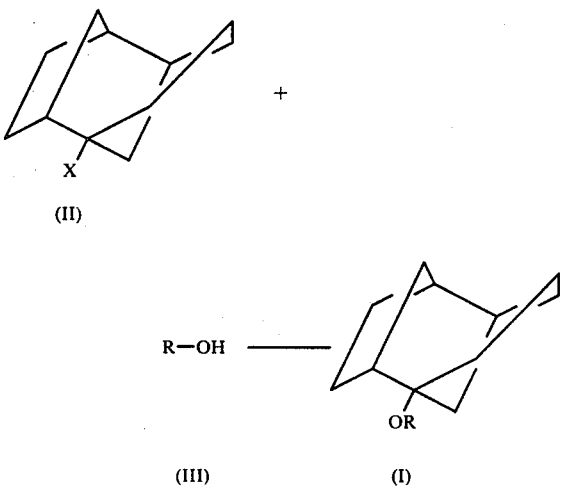

wherein X represents a chlorine or bromine atom, and R is the same as defined above.

The 1-halogenotricyclo[4.3.1.1$^{2,5}$]undecane of the formula (II) is dissolved in anhydrous alcohols of the formula (III), and the resulting mixture is reacted at 50° to 100° C. for 15 minutes to 5 hours to afford the desired compound of the formula (I). Suitable alcohols which are useful include, for example, methanol, ethanol, n-propanol, iso-propanol, n-butanol, sec-butanol, iso-butanol, n-amyl alcohol, iso-amyl alcohol, hexyl alcohol, cyclopentanol and cyclohexanol. When using anhydrous methanol, anhydrous ethanol or anhydrous butanol, the mixture may preferably be refluxed at the boiling point thereof for 0.5 to 2 hours. In the presence of silver oxide as a condensing agent, the reaction proceeds more rapidly. An equivalent or excess amount of the alcohols of the formula (III) may be used relative to the 1-halogenotricyclo[4.3.1.1$^{2,5}$]undecane of the formula (II). Silver oxide as a condensing agent may be used in a wide range of 1 to 50 moles per mole of the 1-halogenotricyclo[4.3.1.1$^{2,5}$]undecane of the formula (II).

The 1-halogenotricyclo[4.3.1.1$^{2,5}$]undecane of the formula (II), the starting material, may be easily produced, for instance, by the bromination of tricyclo[4.3.1.1$^{2,5}$]undecane [J.C.S. Perkin Trans. I, 789 (1975)] with liquid bromine.

The 1-alkoxytricyclo[4.3.1.1$^{2,5}$]undecane of the formula (I) according to the present invention may also be produced, for instance, by hydrolyzing the 1-halogenotricyclo[4.3.1.1$^{2,5}$]undecane of the formula (II) to produce 1-hydroxytricyclo[4.3.1.1$^{2,5}$]undecane, reacting the resulting compound with sodium hydride or the like, and reacting the resulting alkoxide with the corresponding alkyl halide.

The structure of the present compound of the formula (I) thus obtained has been confirmed by the results of its elemental analysis and various spectral data. That is, the molecular formula has been determined by the elemental analysis and mass spectrum, and the existence of an ether bond (1100 cm$^{-1}$) has been confirmed by the infrared absorption spectrum data. Particularly, with respect to its methoxy derivative [R=CH$_3$ in the formula (I)], the characteristic absorption of —OCH$_3$ is observed at 2810 cm$^{-1}$. The absorption at 3010 cm$^{-1}$ due to the C—H stretching vibration characteristic of the carbon skeleton of the tricyclo[4.3.1.1$^{2,5}$]undecane [N. Takaishi et al, J.C.S. Perkin Trans. I. 789 (1975)] indicates that isomerization of the carbon skeleton does not occur during the course of reaction. With further respect to the methoxy and ethoxy derivatives, the characteristic absorptions of —OCH$_3$ (3.15 ppm, s) and —OCH$_2$CH$_3$ (3.40 ppm, q; 1.13 ppm, t) are observed in their $^1$HNMR spectra. The fact that an alkoxy group is bound to the bridgehead position is ascertainable by a singlet absorption in the vicinity of 76 ppm in C$^{13}$nmr.

The 1-alkoxytricyclo[4.3.1.1$^{2,5}$]undecane of the formula (I) according to this invention is a novel compound. 1-Methoxytricyclo[4.3.1.1$^{2,5}$]undecane of the formula (I) (wherein R is a methyl group) has a powerful camphor and somewhat sweet, fruity odor, a camphor-like strong smell. 1-Ethoxytricyclo[4.3.1.1$^{2,5}$]undecane of the formula (I) (wherein R is an ethyl group) possesses a powerful, camphor and somewhat green, leafy odor. 1-n-Butoxytricyclo[4.3.1.1$^{2,5}$]undecane of the formula (I) (wherein R is a n-butyl group) has a sweet woody odor. Therefore, perfume and flavor compositions can be produced with the use of the present compounds.

The compounds according to this invention can be used in the production of perfume compositions for such industrial products as detergents, cleansers, aerosols for insecticides and disinfectants and cosmetics (for example, soaps, lotions, bath additives, ointments, milky lotions, perfumes and au de cologne make-up).

The invention is now described in further detail with reference to several non-limiting Examples. A process for the synthesis of the starting material is hereunder illustrated as a Reference Example.

REFERENCE EXAMPLE

1-Bromotricyclo[4.3.1.1$^{2,5}$]undecane

To 20 ml (387 m mole) of liquid bromine was added 10 g (48 m mole) of tricyclo[4.3.1.1$^{2,5}$]undecane and the resulting mixture was stirred at room temperature for 17 hours. To a cooled saturated sodium hydrogen sulfite solution was added dropwise with stirring the reaction mixture to remove excess bromine. This aqueous solution was extracted twice with a portion of 200 ml of carbon tetrachloride, and the extract was dried over magnesium sulfate. The carbon tetrachloride was evaporated to obtain 19 g of the residue, which was distilled under reduced pressure, and the fraction having a boiling point of 96° to 98° C./2 mmHg was collected. This was a colorless crystalline material having a melting point of 57.5° to 58.5° C.

| Elemental analysis: as C$_{11}$H$_{17}$Br | | | |
|---|---|---|---|
| | C | H | Br |
| Found (%): | 57.2 | 7.4 | 34.2 |
| Calculated (%): | 57.7 | 7.5 | 34.9 |

IR (nujol, cm$^{-1}$): 3030, 1295, 1240, 1155, 1060, 1000, 995, 960, 760.

$^1$HNMR (solvent: CDCl$_3$, internal standard: TMS, δ): 0.8 2.8 (multiplet).

$^{13}$CNMR (solvent: CDCl$_3$, internal standard: TMS, δ): 22.46 (t), 26.52 (t), 27.98 (t+t), 34.27 (t), 37.77 (d), 39.35 (t), 39.80 (d), 41.18 (t), 51.41 (d), 75.08 (s).

MS (relative intensity): 230 (M+), 228 (M+), 150 (13), 149 (100), 107 (15), 91 (15), 83 (18), 81 (44), 79 (23), 67 (18).

EXAMPLE 1

5.0 Grams of 1-bromotricyclo[4.3.1.1$^{2,5}$]undecane obtained as described in the Reference Example was dissolved in 50 ml of anhydrous ethanol, and to the resulting solution was added 5.0 g of silver oxide. After refluxing for 30 minutes and subsequent cooling, the mixture was filtered, and the filtrate was concentrated to obtain a residue, which was distilled to give 3.1 g (yield, 78.8%) of 1-methoxytricyclo[4.3.1.1$^{2,5}$]undecane as a colorless liquid having a boiling point of 89° to 90° C./4 mmHg.

| Elemental analysis: as C$_{12}$H$_{20}$O | | |
|---|---|---|
| | C | H |
| Calculated (%): | 79.94 | 11.18 |
| Found (%): | 80.0 | 11.1 |

IR (neat): 3010, 2810, 1110, 1100, 1085 cm$^{-1}$.
$^1$HNMR (CDCl$_3$) δ: 3.15 (s, —OCH$_3$), 0.9 2.4 (m).
MS: 180 (M+, 11), 137 (100), 112 (31), 111 (99), 109 (46), 79 (33), 67 (29).
$^{13}$CNMR (CDCl$_3$) δc: 20.0 (t), 24.6 (t), 26.6 (t), 28.5 (t), 31.5 (int 2, t+t), 32.0 (t), 35.3 (t), 40.5 (d), 43.0 (d), 47.8 (q), 76.0 (s).

EXAMPLE 2

A mixture of 5.0 g of 1-bromotricyclo[4.3.1.1$^{2,5}$]undecane, 3.0 g of silver oxide and 30 ml of anhydrous ethanol was refluxed for 2 hours. Thereafter, the mixture was treated in the same manner as described in Example 1 to obtain 3.5 g (yield, 82.6%) of 1-ethoxytricyclo[4.3.1.1$^{2,5}$]undecane having a boiling point of 97° to 98° C./4 mmHg.

| Elemental analysis: as C$_{13}$H$_{22}$O | | |
|---|---|---|
| | C | H |
| Calculated (%): | 80.35 | 11.41 |
| Found (%): | 80.4 | 11.3 |

IR (neat): 3020, 1110, 1090, 1080 cm$^{-1}$.
$^1$HNMR (CDCl$_3$): 1.13 (t, —CH$_3$), 3.40 (q, —OCH$_2$CH$_3$), 1.0~2.4 (m).
MS: 194 (M+, 4), 151 (48), 125 (100), 97 (40).
$^{13}$CNMR (CDCl$_3$): 16.4 (q), 20.1 (t), 24.7 (t), 26.7 (t), 28.5 (t), 32.0 (int 2, t+t), 32.5 (t), 35.3 (d), 40.6 (d), 43.5 (d), 55.1 (t), 75.9 (s).

EXAMPLE 3

A mixture of 3.0 g of 1-bromotricyclo[4.3.1.1$^{2,5}$]undecane, 2.0 g of silver oxide and 30 ml of anhydrous n-butanol was refluxed for 6 hours. Thereafter, the mixture was treated in the same manner as described in Example 1, and there was obtained 1.9 g (yield, 65.3%) of 1-n-butoxytricyclo[4.3.1.1$^{2,5}$]undecane having a boiling point of 97° to 98° C./1 mmHg.

| Elemental analysis: as C$_{15}$H$_{26}$O | | |
|---|---|---|
| | C | H |
| Calculated (%): | 81.02 | 11.79 |
| Found (%): | 81.1 | 11.7 |

IR: 3020, 1100, 1090 (s) cm$^{-1}$.
$^1$HNMR (CDCl$_3$) δ: 0.90 (t, —CH$_3$), 3.30 (t, —OCH$_2$CH$_2$—), 0.8~2.7 (m).
MS: 222 (M+, 4), 179 (49), 153 (93), 123 (44), 97 (100), 67 (20).
$^{13}$CNMR (CDCl$_3$): δc (multiplicity): 14.0 (q), 19.6 (t), 20.1 (t), 24.7 (t), 26.8 (t), 28.5 (t), 32.1 (int 2, t+t), 32.4 (t), 33.0 (t), 35.3 (d), 40.5 (d), 43.4 (d), 59.5 (t), 75.7 (s).

EXAMPLE 4

A novel composition possessing a fresh, grassy, leafy odor was produced by adding 100 g of 1-methoxytricyclo[4.3.1.1$^{2,5}$]undecane to 900 g of the following perfume composition:

| Perfume Composition for Herbal Shampoo | |
|---|---|
| Terpinyl acetate | 130 |
| Cedarwood oil | 100 |
| Bergamot oil | 80 |
| Oak moss abs | 60 |
| Amyl salicylate | 60 |
| Coumarin | 60 |
| Galbanum resinoid | 40 |
| Musk ketone | 20 |
| Cedryl acetate | 40 |
| Citronellol | 40 |
| Geraniol | 40 |
| Lavandin oil | 40 |
| Eugenol | 30 |
| Geranyl acetate | 30 |

| Perfume Composition for Herbal Shampoo | |
| --- | --- |
| Geranium oil | 30 |
| Patchouli oil | 25 |
| Neroli oil | 60 |
| Synthetic civet | 15 |
| Dipropylene glycol | 100 |
| | 1000 |

EXAMPLE 5

A novel composition possessing a refreshing odor was produced by adding 50 g of 1-ethoxytricyclo[4.3.1.1$^{2,5}$]undecane to the following composition:

| Perfume Composition for After-shave Lotion | |
| --- | --- |
| Galbanum oil 10% | 120 |
| Bergamot | 100 |
| p-tert-Butyl-cyclohexyl acetate | 100 |
| Cedryl acetate | 100 |
| Methyloctylacetaldehyde | 80 |
| Jasmin oil | 60 |
| Lemon oil | 60 |
| Oak moss abs 50% | 50 |
| Lavandin oil | 60 |
| Clove oil | 50 |
| Neroli oil | 50 |
| Orange oil | 40 |
| Dodecanol 10% | 30 |
| Styralyl acetate | 30 |
| Patchouli oil | 20 |
| Sandalwood oil | 10 |
| α-iso-methylionone | 10 |
| 1,1-Dimethyl-4-acetyl-6-tert-butylindane | 10 |
| | 980 |

The percentage values appearing in the above composition each mean concentrations of a dipropylene glycol solution.

EXAMPLE 6

A novel composition possessing a camphor and somewhat green-leafy odor was produced by adding 20 g of 1-n-butoxytricyclo[4.3.1.1$^{2,5}$]undecane to 980 g of the following perfume composition:

| Perfume Composition for Dentifrice | |
| --- | --- |
| Peppermint oil | 500 |
| Spearmint oil | 200 |
| L-Menthol | 200 |
| Anethole | 100 |
| | 1000 |

What is claimed as intended to be secured by Letters Patent is:

1. A 1-alkoxytricyclo[4.3.1.1$^{2,5}$]undecane represented by the following formula (I),

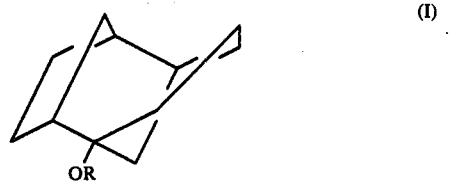

wherein R represents an alkyl group having 1 to 6 carbon atoms or a cycloalkyl group having 5 to 6 carbon atoms.

2. The 1-alkoxytricyclo[4.3.1.1$^{2,5}$]undecane according to claim 1, wherein R in the formula (I) is an alkyl group having 1 to 4 carbon atoms.

3. The compound according to claim 2 where R is methyl.

4. The compound according to claim 2 where R is ethyl.

5. The compound according to claim 2 where R is butyl.